(12) United States Patent
Wight

(10) Patent No.: US 12,410,177 B2
(45) Date of Patent: Sep. 9, 2025

(54) ANTIMICROBIAL AND ANTICANCER CATIONIC PHTHALOCYANINE COMPOUNDS

(71) Applicant: BMG (BRITISH MEDICAL GROUP) LIMITED, Cambridge (GB)

(72) Inventor: Paul Wight, Manchester (GB)

(73) Assignee: BMG (BRITISH MEDICAL GROUP) LIMITED, Cambridge (GB)

( * ) Notice: Subject to any disclaimer, the term of this patent is extended or adjusted under 35 U.S.C. 154(b) by 781 days.

(21) Appl. No.: 17/046,108

(22) PCT Filed: Apr. 9, 2019

(86) PCT No.: PCT/EP2019/058986
§ 371 (c)(1),
(2) Date: Oct. 8, 2020

(87) PCT Pub. No.: WO2019/197419
PCT Pub. Date: Oct. 17, 2019

(65) Prior Publication Data
US 2021/0032261 A1    Feb. 4, 2021

(30) Foreign Application Priority Data
Apr. 9, 2018 (EP) .................... 18166408

(51) Int. Cl.
| C07D 487/22 | (2006.01) |
| A41D 19/00 | (2006.01) |
| A41D 31/30 | (2019.01) |
| C11D 3/16 | (2006.01) |
| C11D 3/48 | (2006.01) |

(52) U.S. Cl.
CPC ....... *C07D 487/22* (2013.01); *A41D 19/0055* (2013.01); *A41D 31/30* (2019.02); *C11D 3/168* (2013.01); *C11D 3/48* (2013.01)

(58) Field of Classification Search
None
See application file for complete search history.

(56) References Cited

U.S. PATENT DOCUMENTS

| 5,486,274 A | 1/1996 | Thetford et al. |
| 2003/0157150 A1 | 8/2003 | Lee |
| 2009/0189086 A1 | 7/2009 | Gessner et al. |
| 2009/0235429 A1 | 9/2009 | Pickard et al. |
| 2010/0221307 A1 | 9/2010 | Matsushita et al. |
| 2011/0145975 A1 | 6/2011 | Eng et al. |
| 2012/0056929 A1 | 3/2012 | Sao et al. |
| 2016/0058921 A1 | 3/2016 | Gros |
| 2016/0159992 A1 | 6/2016 | Foo et al. |
| 2018/0105710 A1 | 4/2018 | Hong et al. |
| 2022/0356364 A1 | 11/2022 | Wight et al. |
| 2022/0363906 A1 | 11/2022 | Wilkinson et al. |
| 2022/0386724 A1 | 12/2022 | Wilkinson et al. |
| 2023/0147289 A1 | 5/2023 | Wight |

FOREIGN PATENT DOCUMENTS

| CN | 1173822 A | 2/1998 |
| CN | 101212987 A | 7/2008 |
| CN | 104003994 A | 8/2014 |
| CN | 104910553 A | 9/2015 |
| CN | 115464988 A | 12/2022 |
| EP | 0000149 | 1/1979 |
| EP | 0003149 | 7/1979 |
| EP | 0815880 A2 | 1/1998 |
| EP | 0906758 | 4/1999 |
| EP | 1356813 | 10/2003 |
| EP | 1444236 B1 | 7/2007 |
| GB | 2279657 A | 1/1995 |
| JP | S54135806 A | 10/1979 |
| JP | H05147127 A | 6/1993 |
| JP | 2005009065 A | 1/2005 |
| JP | 2007118252 A | 5/2007 |
| JP | 2009500462 A | 1/2009 |
| JP | 5885917 B2 | 3/2016 |
| WO | WO 1993/00815 A1 | 1/1993 |
| WO | WO 1998/030094 A1 | 7/1998 |
| WO | 1999/049823 A1 | 10/1999 |
| WO | WO 2003/090744 | * 11/2003 |
| WO | WO 03090744 A1 | 11/2003 |
| WO | WO 2007-000473 | 1/2007 |
| WO | WO 2010/118180 A1 | 10/2010 |
| WO | 2010/138426 A1 | 12/2010 |
| WO | WO 2011012698 A2 | 2/2011 |
| WO | 2015/154543 A1 | 10/2015 |
| WO | WO 2017-148957 | 9/2017 |
| WO | WO 2018/091774 A1 | 5/2018 |

OTHER PUBLICATIONS

Mantareva et al (Bioorg Med Chem 15:4829-4835, 2007) (Year: 2007).*
Woehrle et al (Photochem Photobiol 51:351-356, 1990) (Year: 1990).*
Mack et al (Chem Rev 111:281-321, 2011) (Year: 2011).*
Scalise et al (Bioorg Med Chem 13:3037-3045, 2005) (Year: 2005).*
International Search Report and Written Opinion in corresponding PCT Application No. PCT/EP2019/058986 dated May 29, 2019 (3 pages).
European Search Report in corresponding European Application No. 18166408.7 dated Nov. 22, 2018 (8 pages).
Durmus et al., "The Synthesis, Fluorescence Behaviour and Singlet Oxygen Studies of New Water-Soluble Cationic Gallium(III) Phthalocyanines"—Inorganic Chemistry Communications, Elsevier, Amsterdam, NL, vol. 10, No. 3, (Feb. 15, 2007) pp. 332-338.

(Continued)

*Primary Examiner* — Craig D Ricci
(74) *Attorney, Agent, or Firm* — Foley Hoag LLP; David P. Halstead; Lawrence P. Tardibono

(57) ABSTRACT

Substituted phthalocyanines for the generation of singlet oxygen in which one or more of the substituents bear acationically charged N-alkylated pyridine.

5 Claims, 1 Drawing Sheet

(56) References Cited

OTHER PUBLICATIONS

Medyouni, Rawdha et al., "Synthesis of novel antibacterial metal free and metallophthalocyanines appending with four peripheral coumarin derivatives and their separation of structural isomers," Heterocycles, vol. 87, No. 11, pp. 2283-2297 (2013).

Saki, Neslihan et al., "Synthesis and characterization of novel quaternized 2, 3-(diethylmethylamino)phenoxy tetrasubstituted indium and gallium phthalocyanines and comparison of their antimicrobial and antioxidant properties with different phthalocyanines," Inorganic Chemistry Communications, vol. 95, pp. 122-129 (2018).

Liu, Hong et al. "Synthesis and photophysical/photochemical properties of aryloxy substituted phthalocyanine zinc complex," Chinese Journal of Inorganic Chemistry, vol. 29, No. 3, pp. 486-492 (2013).

Li, Xu-Fei et al. "Photo-generating singlet oxygen by metallophthalocyanines substituted with aromaticoxy group containing nitrogen," Chinese Journal of Applied Chemistry (2007).

* cited by examiner

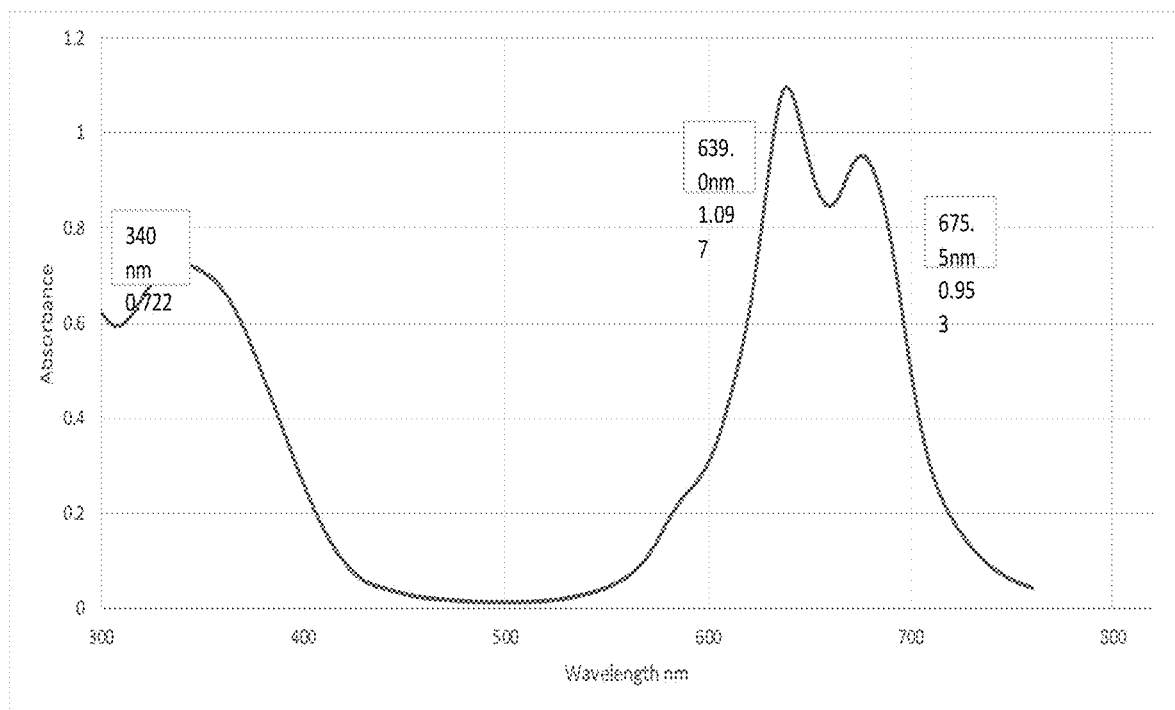

ANTIMICROBIAL AND ANTICANCER CATIONIC PHTHALOCYANINE COMPOUNDS

CROSS-REFERENCE TO RELATED PATENT APPLICATIONS

This is a National Phase of International Application No. PCT/EP2019/058986 filed Apr. 9, 2019, which claims the benefit of European Application No. 18166408.7 filed Apr. 9, 2018. The entire contents of the above-referenced applications are expressly incorporated herein by reference.

FIELD OF INVENTION

The present invention relates to an antimicrobial compound, antimicrobial surfaces comprising the compound, medical gloves comprising the compound, and medical and non-medical uses of the compound.

BACKGROUND ART

Singlet oxygen generators are known to destroy microorganisms. Singlet oxygen has a greater energy than ground-state, triplet oxygen. The singlet and triplet states of oxygen are distinguished by the singlet state having two electrons of anti-parallel spins and the triplet state having an uncoupled pair of electrons with parallel spins. The singlet oxygen is also distinguished from triplet oxygen because it is a highly reactive species with a lifetime from a few microseconds to several hundred microseconds. During its lifetime singlet oxygen has the potential to react before being deactivated, and therefore has a wide number of applications, including antimicrobial applications such as in medical gloves.

Medical gloves are disposable gloves used during medical examinations and procedures that help prevent the spread of infections. They are worn by medical workers at the start of the examination and discarded and destroyed at the end of the procedure. They function by creating a physical barrier between the medical practitioner and patient that prevents the transfer of infectious microorganisms between the two parties. The gloves themselves are not sterile and there is always a danger that the gloves could tear, allowing microorganisms to be transferred between the patient and the practitioner.

US2011/0145975 describes how to coat gloves with an anti-bacterial agent. To get the outside of the glove coated, they have to do the coating in an "offline process", by completing the glove preparation, stripping it from the glove former, then placing it in a tumble dryer equipped with sprayers which coat the glove with the anti-bacterial agent, and then carry out a polymer coating. The polymer coating is required because the anti-bacterial agent is sticky, so there is a need to coat the glove with something to make it usable. Disadvantages are that the anti-bacterial agent is carcinogenic, and does not stay on the gloves, as it leaches off them in use. It also adds a separate process to the manufacturing.

Regardless of the manufacture method, commonly used singlet oxygen generators can still present issues of solubility, aggregation, singlet oxygen generating efficiency, overall unsatisfactory antimicrobial activity and stability.

There is a need therefore to overcome such problems and optimise ease of synthesis, product shelf life, effective and efficient antimicrobial activity as well as safety for the user.

SUMMARY OF THE INVENTION

The present invention provides a compound according to formula 1:

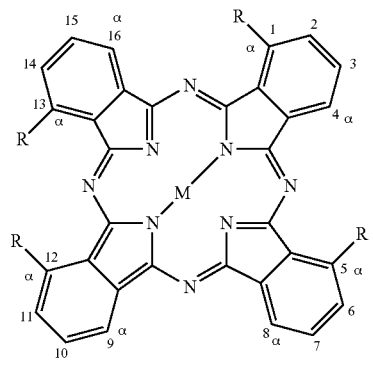

Formula 1

R=R'(a) or R"(b)

R' oxygen linked pyridyl

R" oxygen linked N-alklyated pyridinium wherein:

M is selected from aluminium or zinc,

R" is linked via an oxygen atom to a pyridine group at least 1 of which bears a cationic charge, and the remaining peripheral carbon atoms are an unsubstituted organic radical, a+b=4 b=1 to 4, preferably 1 to 3.9

X=Cl⁻, Br⁻, I⁻, methanesulphonate, ethanesulphonate, formate, acetate or other inorganic or organic counterion or mixture thereof;

and wherein alkylation on the pyridine nitrogen is optionally branched C1-C8 alkyl.

Preferred compounds according to the present invention are:

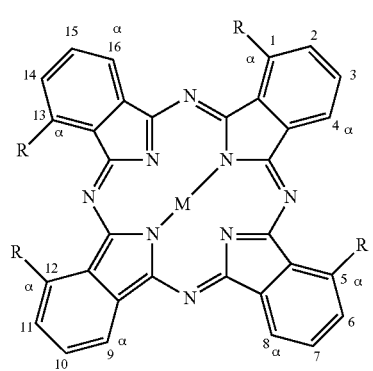

Formula 4

R'(a) or R"(b)

R' 3-oxygen linked pyridyl

R" 3-oxygen linked N-alklyated pyridinium

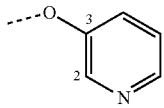

and in particular:

Formula 5

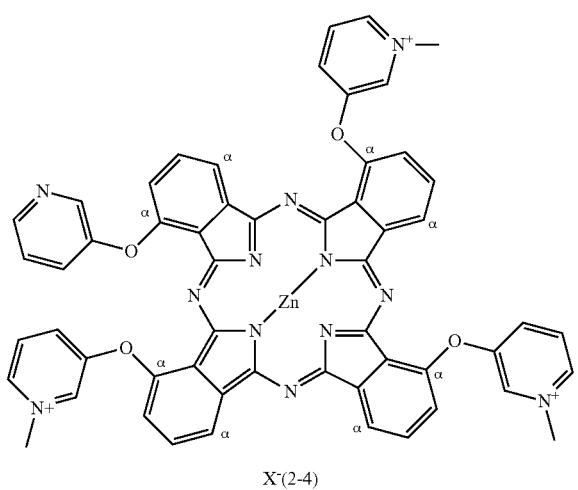

X⁻(2-4)

The present invention also provides an antimicrobial surface or nitrile gloves comprising the compounds.

The present invention also provides the compounds for use in therapeutic methods of treatment, such as in skin and subcutaneous cancers.

The present invention further provides a process for removing stains, wherein the method comprises contacting a stained surface with an aqueous composition of the compounds.

Not only do the compounds of the present invention have effective antimicrobial activity for medical examination gloves, they have numerous other applications such as surface disinfection, cleaning and in human health.

BRIEF DESCRIPTION OF THE DRAWINGS

FIG. 1 shows a UV visible spectrum taken by dissolving 24 mg of the compound in 1000 ml of water, and measuring in a 1 cm path length cell on a Hach-Lange DR3900.

DETAILED DESCRIPTION OF THE INVENTION

The present invention provides novel poly-substituted phthalocyanine compounds which can be used to generate singlet oxygen. The phthalocyanine nucleus may be aluminum or zinc. If aluminium is used, the aluminum may be further substituted by alkyl, aryl, alkoxy, hydroxy or halogen.

Aluminium and zinc are chosen because they are more efficient in generating singlet oxygen than other metals such as copper or nickel, and they are reasonably small and so can be inserted into the phthalocyanine easily, with the reactions occurring under air, in good yield, as opposed to other metals such as using $SiCl_4$, and are easily available in bulk. The central metal atom also influences the position of the absorption maximum of the phthalocyanine, and zinc and aluminium are preferred in the compounds because their absorption is in the visible region of the spectrum especially between 600-700 nm. The zinc compounds described herein are especially preferred.

For the phthalocyanines of the present invention each of the pendant organic radicals linked via oxygen to the phthalocyanine nucleus is independently selected from N-alkylated pyridinium, such that any one phthalocyanine nucleus may carry two or more different organic radicals. Examples of N-alkylated pyridines are 3-hydroxy-1-methylpyridin-1-ium, 3-hydroxy-1-ethylpyridin-1-ium, 3-hydroxy-1-propylpyridin-1-ium.

Further, the phthalocyanines used in the present invention have substituents to the phthalocyanine nucleus in the alpha position, adjacent to the phthalocyanine nucleus. This alpha substitution decreases aggregation of the phthalocyanine. Aggregation is known to reduce singlet oxygen generation efficiency, and therefore this structure prevents aggregation and increases efficiency singlet oxygen generation and hence antimicrobial and other activity. In addition, after extensive research the present inventors have realised the molecules described herein have other desirable properties. They are more thermally stable, and stable to radical degradation than commercially available analogs such as Tinolux BBS and Tinolux BMC.

In the preferred group of compounds the total number of cationic substituents (b) is 2 to 3.9, and more preferably 2.5 to 3.5. The compounds described herein may have a charge of at least +1, and up to +3.9, preferably +2 to +3.9 and most preferably +2.5 to +3.5. Suitable counter-ions for the N-alkylated pyridines include, but are not limited to, iodide, chloride, bromide, methanesulphonate, toluenesulphonate, acetate and hexafluorophosphide.

The phthalocyanines of Formula 1 can be prepared by reacting:

(1) a substituted 1,2-dicyanobenzene of Formula 2:

Formula 2

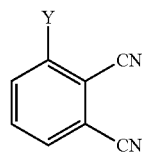

Y = F, Cl, BrI, $NO_2$ wherein Z is selected from chloro, bromo and iodo or nitro and is in the 3 position (alpha) to one of the CN groups, with (2) a compound pyridine-OH whereby the group Z, is replaced by pyridine-O groups to form a compound of Formula (3):

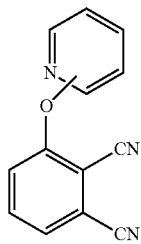

Formula 3

This can then be followed by reaction of one or more 1,2-dicyanobenzene compounds of Formula 3, or a combination of one or more compounds of Formula 3 and 1,2-dicyanobenzene, with an appropriate metal or metal salt optionally in an inert liquid at an elevated temperature to form a phthalocyanine of Formula 1.

Such reactions are fully described in GB 1489394, GB 2200650 and DE 2455675.

In the manufacturing process, the alkylation of the pyridine groups is done last. If the process is not done to completion, some of the pyridyl substituents can remain unalkylated and uncharged. The process can be modified by temperature and stoichiometry to give higher or lower degrees of final alkylation.

The present invention also provides a process for the generation of singlet oxygen by irradiation in the presence of oxygen of the substituted phthalocyanine compounds of the present invention, in which at least one of the peripheral carbon atoms in the 1 or 4, 5 or 8, 9 or 12, 13 or 16 (alpha) positions of the phthalocyanine nucleus, such as shown in Formula 1, is cationic. Suitable sources of electromagnetic radiation include sunlight, tungsten light, fluorescent light, LED lights and lasers with emissions in the 600 to 800 nm region.

Preferable phthalocyanines of the present invention are those which promote the generation of singlet oxygen when exposed to radiation from the 600 to 800 nm region, especially the 630 to 770 nm region of the electromagnetic spectrum.

The reactivity of the singlet oxygen may be utilised in a wide range of applications which includes photobleaching, photodeodorising, photodynamic therapy (PDT), photodynamic inactivation of bacteria, virus, yeasts and other microorganisms, treatment of visible stains on a range of material surfaces, surfaces include fabric, cement, stone, brick, glass, etc., biocidal, degradation of plastics, paper and pulp bleaching, environmental clean-up, anti-microbial action on fibres, incorporation into various products for example in fabrics as deodorisers, into paints or film treatments to destroy microorganisms or contaminants, into cement products, glass products and paints to confer self-cleaning properties, sterilising swimming pools and as a surface treatment to prevent yellowing/discoloration of paper. For photobleaching and photodeodorising application the phthalocyanine compound of the present invention can be incorporated into detergent formulations which are used in a wide range of cleaning applications.

The compound of the present invention can also be used for creating an antimicrobial polymer, especially an elastomer, especially by coagulating a natural or synthetic latex on a former. A process for making an antimicrobial glove can comprise dissolving the compound in an aqueous coagulant and then dipping in a nitrile dispersion.

Gloves are manufactured by dipping glove formers shaped like hands into tanks of liquid latex and admixed chemicals. The latex may contain vulcanization agents that are used to cure the rubber, and a dry rubber film is produced. The formers are first precoated with a coagulant to gel the latex and to facilitate the subsequent removal of the glove from the former. The precoated formers are then dipped in the tanks of chemicals to make the gloves. While still on the formers, the latex gloves can also go through one or more rinses to leach out proteins and residual chemicals. The wet gel is dried and cured in a heated oven and the latex glove cures on the former before they are reversed stripped off the former, packaged, and/or sterilized.

In the manufacturing process of the invention, the singlet oxygen generating compound is designed to dissolve in the aqueous coagulant phase of the above process. The coagulant may contain 10 to 20% of calcium nitrate to coagulate the latex. Typical dyes have several disadvantages in this process, for example they often lack solubility in strong solutions of calcium 2+ ions. The above dye compounds of the present invention, such as recited in Formulas 1, 4 and 5, contain a number of features to allow them to operate in this environment. They are soluble in calcium salts, by virtue of multiple cationic charges. In addition, many latexes, especially nitrile latex are stabilised by anionic carboxyl groups. The dye compounds of the present invention can cross link into the anionic nitrile polymers, bonding to them very strongly, rendering them non leachable. In addition the latex is cured by radical curing at high temperature and many known phthalocyanine dyes, such as Tinolux BBS and Tinolux BMC degrade by radical reactions under these conditions. The dye compounds of the present invention are more thermally stable, and more stable to radical conditions than the Tinolux molecules and therefore are not degraded by the glove forming process.

The dyes of Formula 1 can also be simply dissolved in the aqueous coagulant solution of the glove forming process, by which they are transferred to the surface of the former to the elastomer on dipping, bind irreversibly with it, and create a photo activated antimicrobial surface after curing and drying.

The medical gloves of the present invention can be made of natural or preferably nitrile rubber latex.

The compounds of the present invention can also be used in therapeutic treatment of a human or an animal body, in particular the treatment of skin, subcutaneous cancers, microbial infections or other disease by photodynamic therapy. In such treatment the compound of the present invention can be introduced into the affected tissue and then irradiated with electromagnetic radiation in the region from 600 to 800 nm, preferably 650 to 770 nm in order to generate singlet oxygen which destroys the affected cells. As described above, the phthalocyanine compounds of the present invention can promote the formation of singlet oxygen under the influence of electromagnetic radiation, particularly in the 600 to 770 nm region and are capable of promoting singlet oxygen formation in localised areas.

Measurement of triplet oxygen yields after laser excitation and singlet oxygen emission yields allows calculation of singlet oxygen generating efficiency (SA). The experimental details for these measurements are more fully described in Gorman et al, Journal of the American Chemical Society [1987], 109, 3091; Gorman et al, Journal of the American Chemical Society [1989], 111, 1876 and Gorman et al, Photochemistry and Photobiology 45 (2), 215.

In the synthesis of these materials, a mixture of isomeric structures is obtained, even from a single phthalonitrile. The point group symmetries are C4h, D2h, C2v and Cs, (*J. Mater. Chem. C*, 2015, 3, 10705-10714). Those shown below are typically produced in the ratios 1:1:2:4. All of these structures are incorporated herein.

FIG. 2

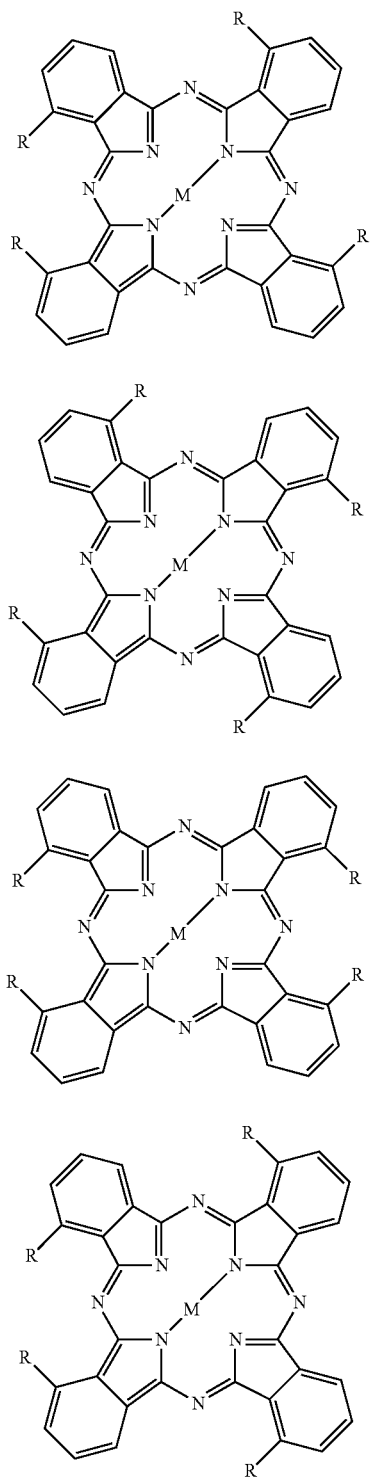

The present invention will now be illustrated, but in no way limited, by reference to the following examples.

EXAMPLES

Example 1-Preparation of Tetrapyridinium Zinc Phthalocyanine (i) Preparation of 3-(pyridin-3-yloxy) phthalonitrile 3-nitrophtalonitrile (1.82 parts) was stirred in DMF 10 parts with 3 hydroxypyridine and potassium carbonate (2.9 parts), heating to 90° C. for 1 hour. The mixture was poured into water, and the greenish solid filtered off.

(ii) Preparation of Tetrapyridine Zinc Phthalocyanine 3-(pyridin-3-yloxy) phthalonitrile (22 parts) was mixed thoroughly with zinc chloride (3.4 parts), urea (1.5 parts), ammonium molybdate (0.04 parts), and DBU (3 parts). The mixture was heated to 180° C. for 30 minutes with stirring, poured into water and the green solid filtered and washed with water.

(iii) Preparation of Tetrapyridinium Zinc Phthalocyanine Iodide Salt

The tetrapyridine zinc phthalocyanine produced above (12.5 parts) was heated in DMSO at 70° C. for 3 hours with an excess (10 parts) of methyl tosylate. The reaction mass was added to water producing a sticky mass. The reaction mass was stirred with lithium iodide (8 parts) to give the iodide salt which was filtered off as a green solid. NMR showed approximately 3:1 quaternised to non-quaternised pyridines.

The UV visible spectrum was taken by dissolving 24 mg of the compound in 1000 ml of water, and measuring in a 1 cm path length cell on a Hach-Lange DR3900, as shown in FIG. 1:

Example 2-Preparation of Tetrapyridinium Aluminium Phthalocyanine (i) Preparation of 3-(pyridin-3-yloxy) phthalonitrile The 3-(pyridin-3-yloxy) phthalonitrile was prepared as above.

(ii) Preparation of Tetrapyridine Aluliminium Phthalocyanine 3-(pyridin-3-yloxy) phthalonitrile (3 parts) was mixed thoroughly with an excess of Aluminium chloride (1 part), and DBU (0.5 parts) in n-pentanol (10 parts). The mixture was heated to reflux at 140° C. for 12 hours with stirring, poured into water:methanol 1:1 (10 parts) and the green solid filtered.

(iii) Preparation of Tetrapyridinium Aluminium Phthalocyanine Iodide Salt

The tetrapyridine aluminium phthalocyanine produced above (12.5 parts) was heated in DMSO at 70° C. for 3 hours with an excess (10 parts) of methyl tosylate. The reaction mass was added to water producing a sticky mass. The reaction mass was stirred with lithium iodide (8 parts) to give the iodide salt which was filtered off as a green solid. NMR showed approximately 3:1 quaternised to non-quaternised pyridines.

Example 3—Preparation of an Antimicrobial Elastomer 0.25 parts of the compounds from example 1 were dissolved in 5100 parts of water, containing 1500 parts of calcium nitrate. To the mixture was added 0.8 part of a calcium stearate mold release agent. A porcelain former heated to 150° C. was dipped in the coagulant and dried in an oven at 150° C. for 15 minutes. The dried former was dipped in a nitrile latex suspension (Nantex 672), cured and dried. The glove was stripped from the former and the glove surface was tested according to ASTM D7907. *Staphylococcus aureus* was reduced by >log 5 in 5 minutes. The glove making process is described more fully in U.S. Pat. No. 8,936,843 B2 and references disclosed therein.

Example 4—Alternative Preparation of Tetrapyridinium Zinc Phthalocyanine (i) Preparation of 3-(pyridin-3-yloxy) phthalonitrile The 3-(pyridin-3-yloxy) phthalonitrile was prepared as described in J Organomet Chem. 2009 May 1; 694 (11): 1607-1611.

(ii) Preparation of Tetrapyridine Zinc Phthalocyanine

To 2-ethylhexanol (242 parts) was added to 3-(pyridin-3-yloxy)-phthalonitrile (145 parts) followed by zinc chloride (21 parts) and DBU (parts Kg). The reaction was heated to 150° C. to effect cyclisation, then cooled and crystallised with iso-propanol (1600 parts). The product was filtered, washed with further iso-propanol and dried to give the pyridyloxy zinc phthalocyanine.

(iii) Preparation of Tetrapyridinium Zinc Phthalocyanine Iodide Salt

To N-Methyl-2-pyrrolidone (NMP) was added the pyridyloxy zinc phthalocyanine (140 parts) and methyl tosylate (120 parts). The mixture was heated to effect quaternisation, then cooled and mixed with iso-propanol (3100 parts) containing lithium iodide (160 parts). The product was filtered, washed with further iso-propanol and dried to give the quaternised zinc phthalocyanine as predominantly the iodide salt.

Further examples as shown below were also prepared:

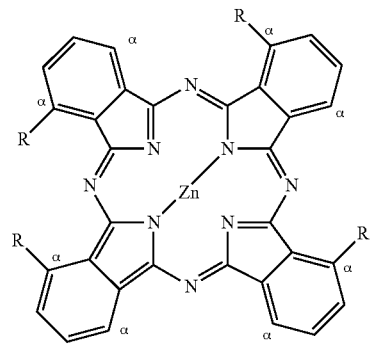

| Example | 4 | 5 | 6 | 7 | 8 | 9 |
|---------|---|---|---|---|---|---|
| Metal | Zn | Zn | Zn | Al | Al | Al |
| R | | | | | | |
| R' | a = 1, b = 3 | a = 1, b = 3 | a = 1, b = 3 | a = 1, b = 3 | a = 1, b = 3 | a = 1, b = 3 |

The invention claimed is:
1. A population of compounds comprising compounds according to one or more of formulas $C_s$, $C_{4h}$, $D_{2h}$ and $C_{2v}$ below:

$C_s$

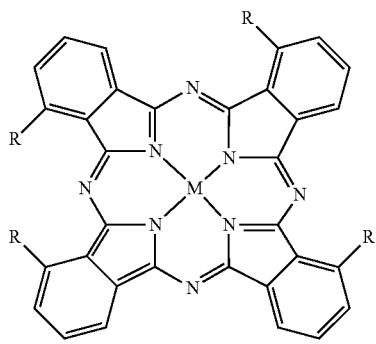

$C_{4h}$

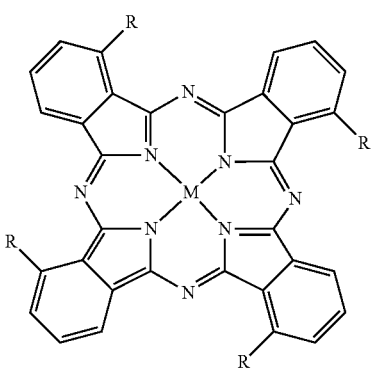

$D_{2h}$

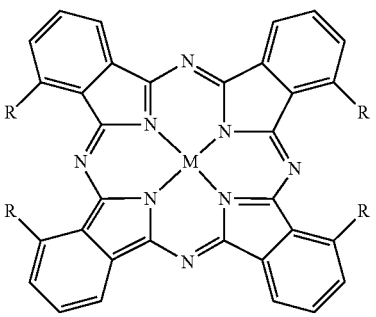

$C_{2v}$

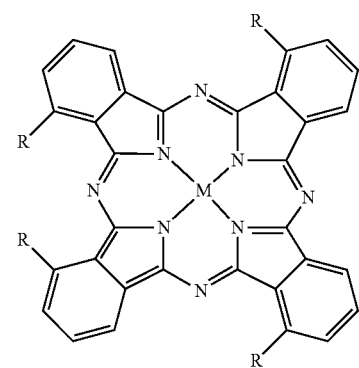

wherein in each of the above formulas:
each occurrence of R is independently R' or R", where there is a mean average of (a) occurrences of R' and (b) occurrences of R" in each formula; and a+b=4;

R' is 3-oxygen linked pyridyl having the following structure:

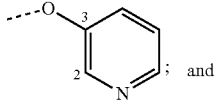

R" is 3-oxygen linked N-alkylated pyridinium having the following structure:

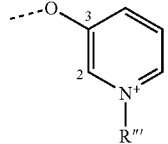

wherein the mean average total number of substituent R" (b) is from 1 to 3.9;
M is selected from aluminium or zinc;
each formula has counterions X selected from Cl⁻, Br⁻, I⁻, methanesulphonate, ethanesulphonate, formate, acetate or other inorganic or organic counter-ion or mixture thereof; and
wherein R'" is optionally branched C1-C8 alkyl,
and wherein the population of compounds comprises a compound having the following structure:

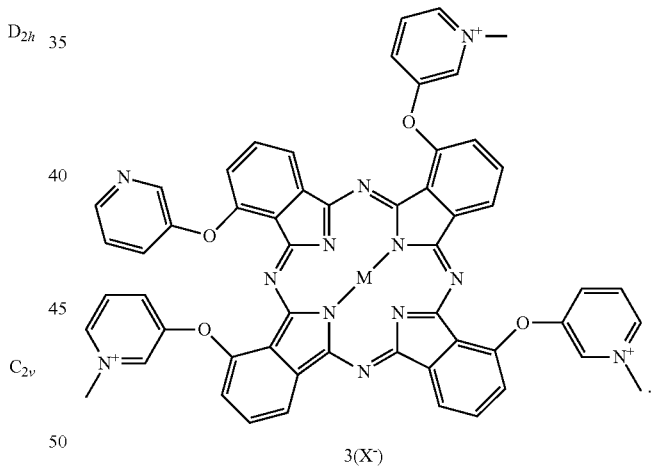

2. A population of compounds according to claim 1, wherein in each of formulas $C_s$, $C_{4h}$, $D_{2h}$ and $C_{2v}$ the mean average total number of R" substituents (b) is from 2 to 3.

3. A population of compounds according to claim 1, which absorbs electromagnetic radiation at a wavelength from 600 to 800 nm.

4. A population of compounds according to claim 1, wherein in each of formulas $C_s$, $C_{4h}$, $D_{2h}$ and $C_{2v}$ the mean average total number of R" substituents (b) is from 2.5 to 3.

5. A nitrile glove comprising the population of compounds according to claim 1.

* * * * *